United States Patent [19]

Brighton et al.

[11] Patent Number: 4,467,808
[45] Date of Patent: Aug. 28, 1984

[54] METHOD FOR PREVENTING AND TREATING OSTEOPOROSIS IN A LIVING BODY BY USING ELECTRICAL STIMULATION NON-INVASIVELY

[75] Inventors: Carl T. Brighton, Malvern; Solomon R. Pollack, Dresher, both of Pa.

[73] Assignee: Biolectron, Inc., Hackensack, N.J.

[21] Appl. No.: 419,431

[22] Filed: Sep. 17, 1982

[51] Int. Cl.³ .............................................. A61N 1/06
[52] U.S. Cl. ................................................ 128/419 F
[58] Field of Search ............... 128/419 R, 419 F, 422, 128/82.1

[56] References Cited

U.S. PATENT DOCUMENTS

| | | | |
|---|---|---|---|
| 3,783,880 | 1/1974 | Kraus | 128/82.1 |
| 3,893,462 | 7/1975 | Manning | 128/419 F |
| 3,902,502 | 9/1975 | Liss et al. | 128/422 |
| 3,989,050 | 11/1976 | Buchalter | 128/419 R |
| 4,055,190 | 10/1977 | Tany | 128/422 |
| 4,093,975 | 6/1978 | Roberts | 128/422 |
| 4,154,240 | 5/1979 | Ikuno et al. | 128/422 |
| 4,237,898 | 12/1980 | Whalley | 128/422 |
| 4,249,537 | 2/1981 | Lee et al. | 128/422 |
| 4,315,503 | 2/1982 | Ryaby et al. | 128/82.1 |

OTHER PUBLICATIONS

Lavine et al., "The Influence of Electric Current on Bone Regeneration in Vivo", *Acta Orthop. Scandinav.*, vol. 12, pp. 305-315, 1971.
McElhaney, J. H. et al., Electric Fields and Bone Loss of Disuse, *J. Biomechanics*, vol. 1, pp. 47-52, Pergamon Press, 1968.

*Primary Examiner*—William E. Kamm
*Assistant Examiner*—Mitchell J. Shein
*Attorney, Agent, or Firm*—Brumbaugh, Graves, Donohue & Raymond

[57] ABSTRACT

Osteoporosis in a living body prevented and/or treated by applying electrodes non-invasively to a body and supplying to the electrodes an AC signal of about 5-15 volts peak-to-peak at a frequency of about 20-100 KHz to cause a treatment current to flow in a body region affected or likely to be affected by osteoporosis.

8 Claims, 13 Drawing Figures

METHOD FOR PREVENTING AND TREATING OSTEOPOROSIS IN A LIVING BODY BY USING ELECTRICAL STIMULATION NON-INVASIVELY

TECHNICAL FIELD

This invention relates to a method of preventing and treating osteoporosis in a living body using non-invasive techniques, and more particularly to treating a region affected by osteoporosis by inducing a current to flow in the region affected.

BACKGROUND OF THE INVENTION

Bones comprise an organic component (cells and matrix), and an inorganic or mineral component. The cells and matrix comprise a framework of collagenous fibers which is impregnated with the mineral component, chiefly calcium phosphate (85%) and calcium carbonate (10%), which imparts the quality of rigidity to bone. In a disease commonly known as osteoporosis, the bone demineralizes and becomes abnormally rarefied. While osteoporosis in general predominantly afflicts the elderly, a specific form of osteoporosis known as disuse or immobilization osteoporosis has been identified with immobilized persons of all ages whose bones are not subject to functional stress. In these cases, some patients will experience significant loss of cortical and cancellous bone during prolonged periods of immobilization. Quite often, an elderly patient immobilized after a fracture of a long bone may experience bone loss due to disuse, which may ultimately lead to secondary fractures in an already osteoporotic skeleton. Diminished bone density may lead to verterbrae collapse, fractures of the hips, lower arms, wrists, ankles and incapacitating pain.

Attempts at treating and/or preventing osteoporosis by means of electrical signals include the work of McElhaney and Stalnaker who in 1967 reported that a 200 V and 30 Hz field applied between two parallel plates to a cast-immobilized femur of the rat could reduce the bone weight loss and bone cortical area reduction associated with immobilization. However the number of animals was too small to yield results of statistical significance.

Experiments using signals of the same frequency were repeated in 1978 by Martin and Gutman who found statistically significant increases in the weight (ash weight) and in the cross-sectional area of stimulated femora on one leg of a rat relative to unstimulated femora on the other leg. Their experiments utilized parallel plates applied to the cast-immobilized hind limb of rats, with an electrical signal of 100 v/cm at 30 Hz applied to the plates for periods of 2 to 8 hours per day. Some positive results were obtained, and an increase in stimulation times was shown to improve the results.

Kenner in 1975 showed that Pt-10% Rh electrodes implanted one centimeter apart in the heel of an eight week old male New Zealand rabbit whose legs were immobilized by casting could prevent bone loss due to disuse when measured by graded histologic bone sectors. These results were observed using both constant DC and pulsed DC stimulation signals. Further, Bassett showed that an inductively coupled electric field could enhance the mechanical strength of embedded rat tibia as measured by compression in a plunger load-cell apparatus.

Thus, prior work at treating and/or preventing osteoporosis has included the use of relatively high amplitude voltage signals, necessitating high power sources. Further, the stimulation signals used have been limited to constant or pulsed DC signals, or AC signals of relatively low frequency. Lastly, the results of this prior work has in some cases been inconclusive and discouraging.

SUMMARY OF THE INVENTION

In accordance with the present invention, osteoporosis in a living body is treated and/or prevented by applying a low voltage AC stimulation signal in the ultrasonic frequency range of about 20 to 100 KHz across electrodes non-invasively applied to positions on a subject's body. In this way, a treatment current is caused to flow in the region affected by osteoporosis for a period of time and either a reduction in the rarefication of bone mass or an increase in bone mass is effected.

For a better understanding of the above and other features and advantages of the invention, reference is made to the following detailed description of a preferred procedure according to the invention taken in conjunction with the following drawings.

DESCRIPTION OF THE PREFERRED EMBODIMENT

Figure 1:
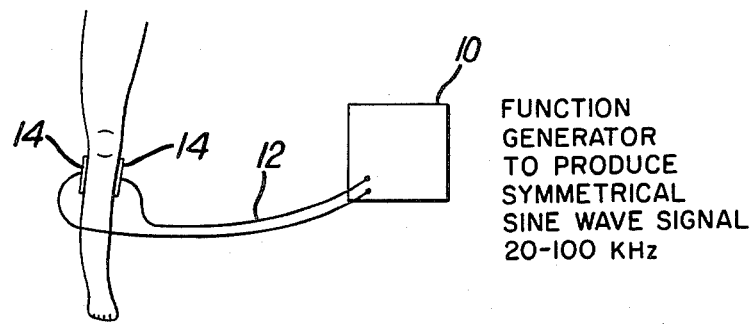
FIG. 1 is a simplified schematic representation of a signal generating system coupled non-invasively with a living body for the application of a treatment signal to a treatment area affected by osteoporosis.

While this invention may be practiced in many different forms, there is shown in the drawings and will herein be described in detail one specific method, with the understanding that the present disclosure is to be considered as an exemplification of the principles of the invention and is not intended to limit the invention to the precise method illustrated.

Shown in FIG. 1 is a signal frequency generator 10 which generates an AC stimulation signal having a frequency within the ultrasonic frequency range (e.g. 20 to 100 KHz). The AC stimulation signal is preferably an unmodulated symetrical sine wave having a peak-to-peak amplitude within the range of about 5 to 10 volts. The frequency generator 10 may be a Wave Tech Model 148 Function Generator, for example. A cable 12 supplies the stimulation signal to a pair of stimulation electrodes 14 non-invasively applied to a treatment area of a living body at positions such that a current is caused to flow in the body region affected by osteoporosis.

Since osteoporosis afflicts different areas of the body, e.g. the vertebrae, hips, lower arms, wrists and ankles, the electrodes should preferably be positioned relatively close to the particular body region affected. However, the electrodes may be applied at locations remote from the region affected by osteoporosis, where that proves necessary or desirable because of the particular region affected. Thus, if the region affected is in a body limb, the electrodes may be positioned at a location fairly proximate to the affected region, but in the case of the vertebrae, it may be necessary or desirable to place the electrodes remote from the vertebrae.

In order to achieve good electrical contact, the skin of the patient should be shaved to remove any hair, and a suitable conducting material such as K-Y lubricating jelly (Johnson & Johnson) can be applied to the skin before placing the electrode there on. If stimulation is to be continued more than several days, the skin can be reshaved and fresh K-Y gel applied. While the electrodes 14 are preferably made of bare metal, one or both may be coated with dielectric material such as Mylar film.

EXAMPLES

The efficacy of the method according to the invention both for preventing and treating existing osteoporosis, has been established clinically as follows:

PREVENTION OF OSTEOPOROSIS

A total of 40 Wistar rats each weighing about 125 grams were anesthetized with 0.1 cc (5 m.g.) Neumbutal, and then the hip and greater trochanter portions of their right hind limb were shaved. A 2 cm transverse incision was made over the anatomic landmark, the sciatic nerve was located and bathed in 1% lidocaine with 1:1000 epinoehrine. The sciatic nerve was then gently lifted and a 0.5 cm segment was excised. The overlying fascia and skin was closed with 3-0 interrupted silk sutures and the right hind limb was then sewn to the abdominal skin with 3-0 silk suture to prevent dragging and injury to the denervated limb. An Elizabethan collar made of a circle of corrugated cardboard was placed around each animal's neck to the rear of the forelimbs to minimize the animal's interference with its hind limb area. The animals were then placed in recovery receptacles.

On the second post-operative day, stainless steel electrodes 14 which were 1.5 cm in diameter were placed over the medial and lateral aspects of the right mid-tibia in each animal and then taped in place with a suitable material such as moleskin tape. Lead wires from the electrodes 14 were secured to the right hind limb and the abdomen of each animal by suitable means such as Velcro tape. The lead wires were brought out through the top of the cage, and tension on the lead wire was maintained using a weight and pulley arrangement to minimize animal interference with the lead wires.

Electrical Stimulation

The 40 animals were divided into five groups of seven animals each. One group served as a control group and received no electrical stimulation signals (even though they were fitted with electrodes 14), and the other four experimental groups were continuously stimulated with a 60 KHz symmetrical sine wave signal from the signal generator 10 (FIG. 1) for 24 hours a day for 12 consecutive days. The amplitude of the sine wave signal was 2.5 volts peak-to-peak for experimental group 1, 5.0 volts for group 2, 7.5 volts for group 3 and 10.0 volts for group 4. The signal was monitored by a Tektron oscilloscope from 8 a.m. to 6 p.m. daily. Electrodes that had been displaced or torn were replaced daily and animals that had gotten loose during the evening were promptly restrained and stimulation resumed the next morning.

On the 12th day, all 40 of the animals were sacrificed using ether, and both the right and left tibia and femur of each animal were excised and cleaned of muscle, tendon, and periosteum.

Biomechanical and Weight Analysis

The tibiae and femora of the remaining 35 animals were preserved in Hank's medium, and were weighed wet and measured in the longitudinal direction immediately. On the same day, the breaking strength of each specimen was determined by the cantilever bending method on the CGS-Lawrence apparatus. Records of the load versus angular deformation for each specimen were obtained. In the tibia, the fibular remnant was used for orientation of the specimen. The right tibiae were oriented in the jig with the fibular remnant facing the tester, while the left-sided tibiae were oriented with the fibular remnant facing away from the tester. In the femur, the femoral head was used for orientation. The right femur had the femoral head oriented in the base of the jig away from the tester while the left femur had the femoral head facing the tester. Each specimen was cantilever bent to failure and the maximum (ultimate) stress value was recorded.

Thereafter, each specimen was dried in a Lab-Line Heat Cab at 100° for twenty-four hours and reweighed (to obtain dry weight), and then ashed in a Muffle furnance at 700° for forty-eight hours and reweighed (to obtain ash weight). While wet weight, dry weight and ash weight measurements were made for each specimen, ash weight is believed to provide the best indicator of bone mass.

The tibial data for all the animals in each of the five groups was averaged and appears in Table I, and the femoral data was similarly averaged and appears in Table II.

TABLE I

EXPERIMENT I
PREVENTION OF DISUSE OSTEOPOROSIS USING VARIOUS AMPLITUDE
VOLTAGE STIMULATION SIGNALS
TIBIAL DATA
(N = 7 IN EACH GROUP)

| R | L | R/L | R | L | R/L | R | L | R/L |
|---|---|-----|---|---|-----|---|---|-----|
| Control | | | Experimental | | | | | |

TABLE I-continued
EXPERIMENT I
PREVENTION OF DISUSE OSTEOPOROSIS USING VARIOUS AMPLITUDE VOLTAGE STIMULATION SIGNALS
TIBIAL DATA
(N = 7 IN EACH GROUP)

| | R | L | R/L | R | L | R/L | R | L | R/L |
|---|---|---|---|---|---|---|---|---|---|
| | 0 Volts | | | 2.5 Volts | | | 5.0 Volts | | |
| Wet Wt. | 0.44523 | 0.57150 | 0.77468 | 0.74259 | 0.76870 | 0.96865 | 0.60062 | 0.50977 | 1.18814 |
| | ±0.11930 | ±0.08006 | ±0.15322 | ±0.09257 | ±0.06397 | ±0.12380 | ±0.06236 | ±0.07897 | ±0.09797 |
| | $p < .01$ | | | NS | | $p < .05$ | $p < .001$ | | $p < .001$ |
| Dry Wt. | 0.17831 | 0.21927 | 0.81873 | 0.20017 | 0.23019 | 0.87264 | 0.26017 | 0.22920 | 1.14051 |
| | ±0.02472 | ±0.03354 | ±0.09284 | ±0.00635 | ±0.017 | ±0.05097 | ±0.04637 | ±0.03834 | ±0.15719 |
| | $p < .01$ | | | $p < .001$ | | NS | $p < .01$ | | $p < .01$ |
| Ash Wt. | 0.09637 | 0.11567 | 0.84411 | 0.10256 | 0.12423 | 0.82677 | 0.11334 | 0.10881 | 1.04977 |
| | ±0.00712 | ±0.01819 | ±0.08928 | ±0.00514 | ±0.00805 | ±0.03260 | ±0.00839 | ±0.01026 | ±0.13079 |
| | $p < .01$ | | | $p < .001$ | | NS | NS | | $p < .01$ |
| Ultimate Stress | 11.00 | 15.06 | 0.73 | | | | 15.39 | 14.64 | 0.97 |
| | ±1.21 | ±0.44 | ±0.08 | | | | ±0.29 | ±0.86 | ±0.04 |
| | $p < .01$ | | | | | | NS | | $p < .05$ |
| | | | | 7.5 Volts | | | 10.0 Volts | | |
| Wet Wt. | | | | 0.81643 | 0.70633 | 1.15788 | 0.70429 | 0.56153 | 1.26422 |
| | | | | ±0.13492 | ±0.09048 | ±0.14396 | ±0.07351 | ±0.06964 | ±0.15851 |
| | | | | $p < .02$ | | $p < .01$ | $p < .001$ | | $p < .01$ |
| Dry Wt. | | | | 0.22136 | 0.20871 | 1.06589 | 0.24230 | 0.20304 | 1.20173 |
| | | | | ±0.02174 | ±0.02520 | ±0.08662 | ±0.03178 | ±0.023 | ±0.18187 |
| | | | | $p < .05$ | | $p < .01$ | $p < .01$ | | $p < .01$ |
| Ash Wt. | | | | 0.11286 | 0.11431 | 0.98778 | 0.12246 | 0.10187 | 1.20588 |
| | | | | ±0.01095 | ±0.00900 | ±0.06508 | ±0.02104 | ±0.01281 | ±0.16150 |
| | | | | NS | | $p < .01$ | $p < .01$ | | $p < .01$ |
| Ultimate Stress | | | | | | | 14.94 | 14.93 | 1.01 |
| | | | | | | | ±0.78 | ±0.27 | ±0.0 |
| | | | | | | | | NS | $p < .02$ |

TABLE II
EXERIMENT 1
PREVENTION OF DISUSE OSTEOPOROSIS USING VARIOUS AMPLITUDE VOLTAGE STIMULATION SIGNALS
FEMORAL DATA
(N = 7 IN EACH GROUP)

| | R | L | R/L | R | L | R/L | R | L | R/L |
|---|---|---|---|---|---|---|---|---|---|
| | Control (0 Volts) | | | Experimental 2.5 Volts | | | 5.0 Volts | | |
| Net Wt. | 0.87819 | 0.84254 | 0.99917 | 1.00594 | 1.01058 | 1.00249 | 0.67903 | 0.65109 | 1.04096 |
| | ±0.03945 | ±0.15169 | ±0.17193 | ±0.09447 | ±0.09157 | ±0.13122 | ±0.09287 | 0.06164 | ±0.06862 |
| | NS | | | NS | | NS | NS | | NS |
| Dry Wt. | 0.22529 | 0.25791 | 0.87110 | 0.23227 | 0.27599 | 0.83970 | 0.28997 | 0.27000 | 1.10448 |
| | ±.03922 | ±0.02335 | ±0.11836 | ±0.05235 | ±0.05929 | ±0.02772 | ±0.05200 | ±0.06852 | ±0.22531 |
| | $p < .02$ | | $p < .001$ | NS | | NS | $p < .05$ | | |
| Net Wt. | 0.11050 | 0.12954 | 0.85577 | 0.11357 | 0.15574 | 0.76003 | 0.11050 | 0.11754 | 0.95003 |
| | ±0.01983 | ±0.01415 | ±0.15372 | ±0.00445 | ±0.04319 | ±0.13193 | ±0.01567 | ±0.01551 | ±0.15002 |
| | $p < .02$ | | | $p < .02$ | | NS | NS | | NS |
| | | | | 7.5 Volts | | | 10.0 Volts | | |
| Net. Wt. | | | | 0.88873 | 0.89259 | 0.99989 | 0.98997 | 0.79479 | 1.24180 |
| | | | | ±0.11282 | ±0.06768 | ±0.13969 | ±0.20090 | ±0.07757 | ±0.17626 |
| | | | | NS | | NS | NS | | $p < .01$ |
| Dry Wt. | | | | 0.23969 | 0.27413 | 0.87678 | 0.26774 | 0.25699 | 1.04662 |
| | | | | ±0.01372 | ±0.01934 | ±0.06260 | ±0.03921 | ±0.02290 | ±0.17114 |
| | | | | $p < .002$ | | NS | NS | NS | $p < .05$ |
| Net Wt. | | | | 0.11434 | 0.13846 | 0.82872 | 0.10647 | 0.12100 | 0.88088 |
| | | | | ±0.00625 | ±0.01096 | ±0.05599 | ±0.01463 | ±0.01307 | ±0.09417 |
| | | | | $p < .001$ | | NS | $p < .01$ | | NS |

In addition to the data provided for the tibia and femur for each leg, a ratio of right/left (R/L) was calculated for wet, dry and ash weight for both tibia and femur for each of the five groups.

As mentioned, only the right tibia of each experimental animal was stimulated. However, by measuring both the right and left tibiae and femora in each animal and by calculating a ratio of right/left for each pair of tibiae and femora in each animal, control for any growth or disease mechanisms that might be naturally occurring in the animal was obtained.

Figure 2:
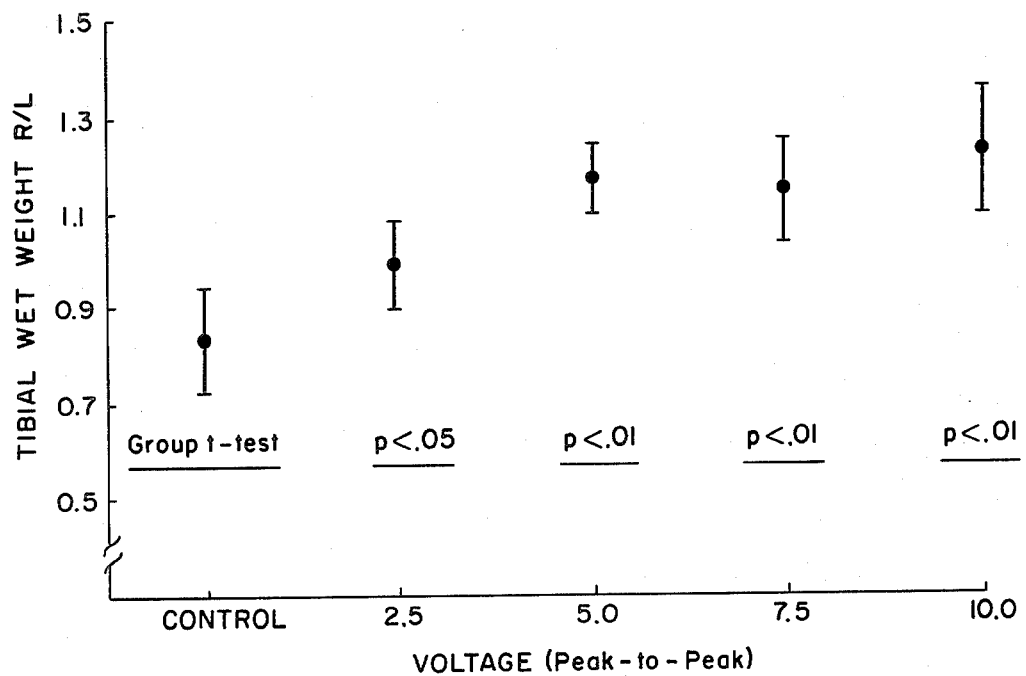
FIGS. 2-4, inclusive are graphs showing respectively, the tibial wet weight, the tibial dry weight and the tibial ash weight (ratio of right/left) for an unstimulated control group and four stimulated groups treated in accordance with the invention.

Results of electrical stimulation with a 60 KHz low voltage signal yielded statistically significant responses in all categories, namely, wet weight, dry weight, ash weight, and ultimate stress. Tibial wet weight was enhanced in the right neurectomized limb at all voltages (i.e. 2.5, 5.0, 7.5 and 10.0 volts) when plotted as R/L ratio, and compared by means of a "group t" test to the free-roaming control animals fitted with electrodes but not stimulated. (See FIG. 2). As can be seen from FIG. 2 and Table I, the observed response generally increases with increasing voltage. At 5.0 volts an actual increase in bone mass (wet weight) of the stimulated right side relative to its non-immobilized control was obtained.

Thus, not only was osteoporosis (loss of bone mass) effectively prevented, at 5.0 volts, but an actual increase in bone mass was experienced. Bone mass increase was exhibited even more so at 7.5 volts and 10 volts.

Figure 3:
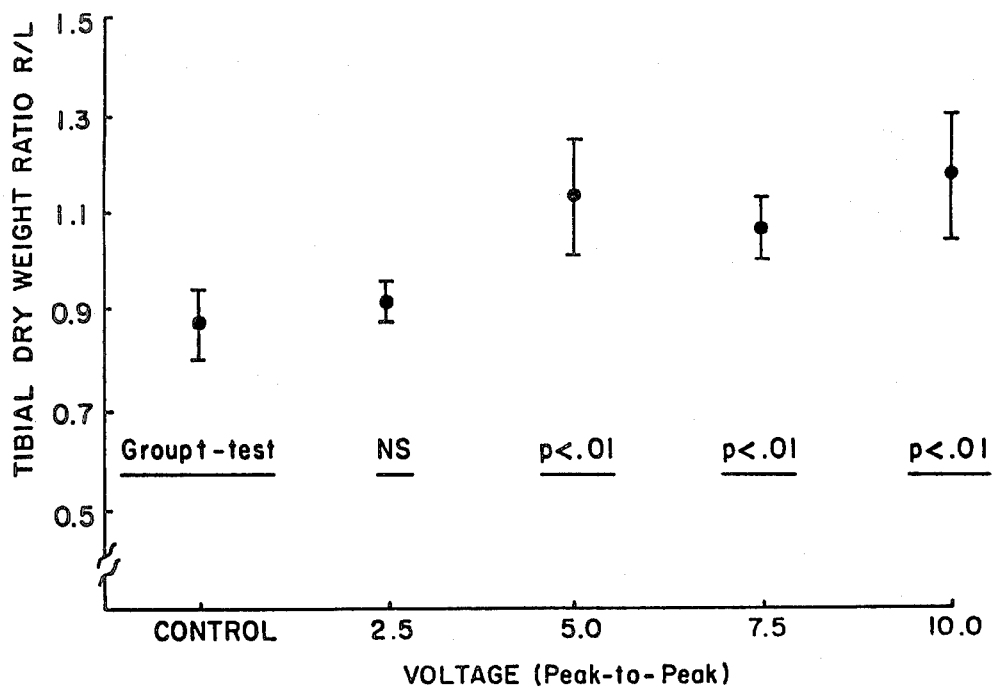
Figure 4:
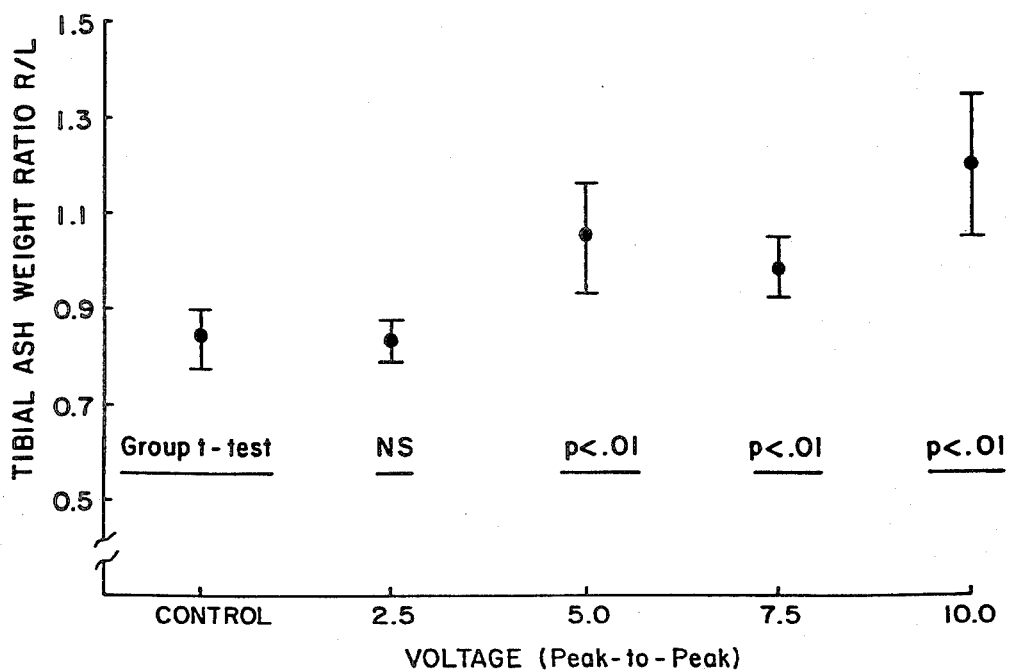

The data for the tibial dry weight exhibits a similar response to that seen in the tibial wet weight data. As can be seen in FIG. 3, tibial dry weight exhibits a threshold point with no significance at 2.5 volts and significance thereafter at 5.0 volts, 7.5 volts, and 10.0 volts. Bone mass increase is also apparent from the tibial dry weight data at 5.0 volts and 10.0 volts. As seen in FIG. 4, the data for tibial ash weight exhibits statistical significance beginning at 5.0 volts, with some bone mass increase apparent at 5.0 volts and even more increase at higher voltages.

Figure 5:
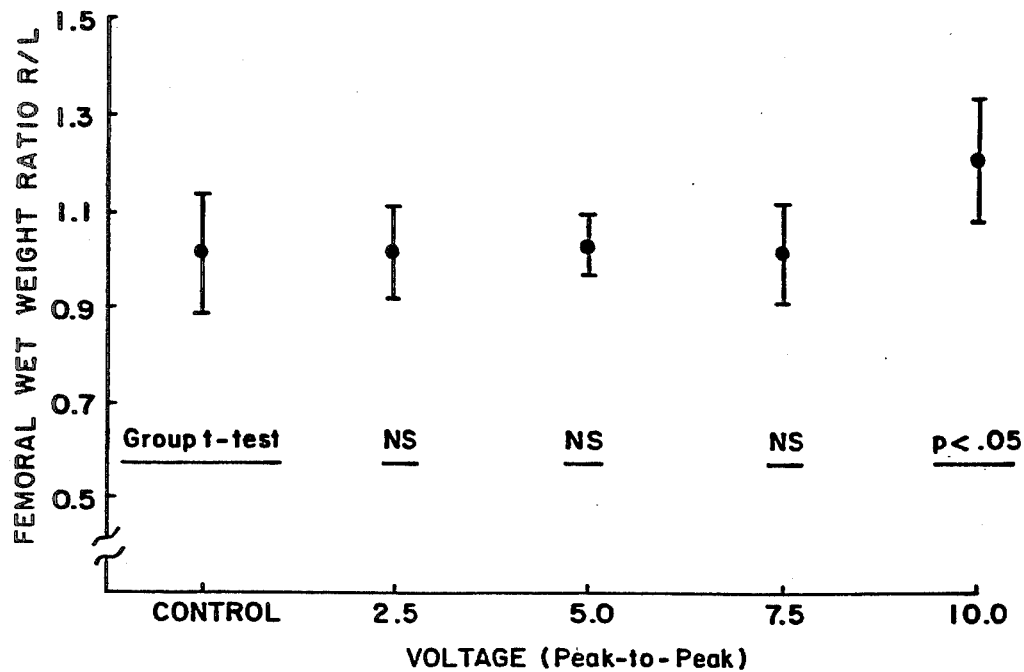
FIGS. 5-7, inclusive, are graphs showing respectively, the femoral wet weight, the femoral dry weight, and the femoral ash weight (ratio of right/left) for the control group (unstimulated) and for all four stimulated groups that were treated according to the invention.
Figure 6:
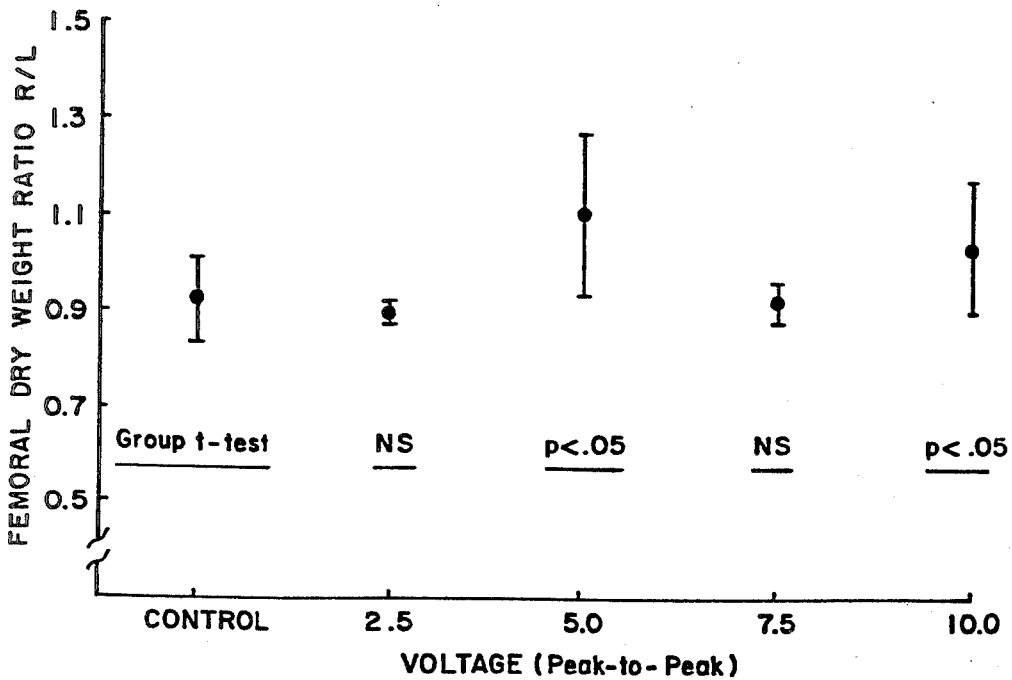
Figure 7:
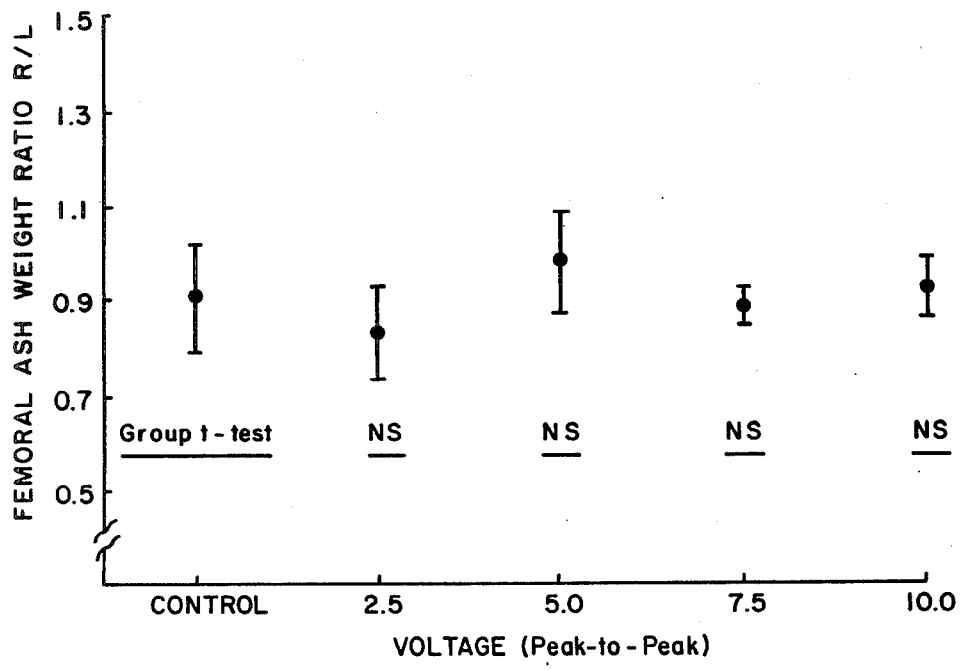

By studying the effect that stimulation of the tibia has on the femur of the same leg, one can see that the treatment is fairly localized. As one can see in Table II and FIG. 5, femoral wet weight is enhanced in a statistically significant manner only at 10 volts. Similarly, FIG. 6 shows that femoral dry weight is significant only at 5.0 volts and 10.0 volts. Femoral ash weight, as seen in FIG. 7, was not significantly changed with any of the voltages.

Figure 8:
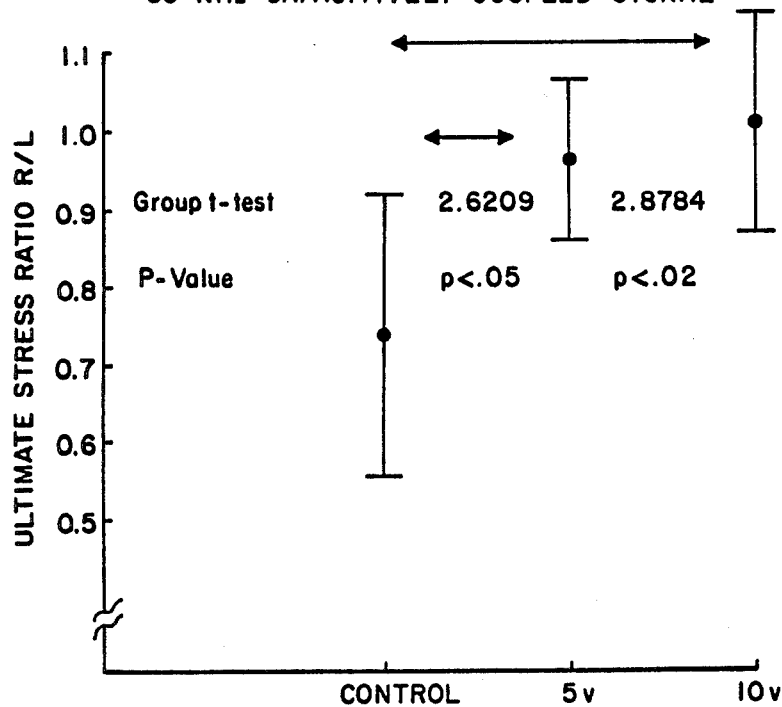
FIG. 8 is a graph showing the tibial ultimate stress (ratio of right/left) for the unstimulated control group and for two stimulated groups that were treated according to the invention.

The result of the cantilever bending experiment (ultimate stress of the tibiae) is represented in FIG. 8. The ultimate stress is clearly enhanced in the 5.0 volt and 10.0 volt groups. This enhancement is statistically significant and shows an incremental response with increased voltage.

From a histological analysis, the stimulated tibiae exhibited a periosteal reaction with the periosteum being lifted off of the cortex. Beneath the periosteum, cartilage could be seen proliferating. As one progressed away from the periosteum, the cartilage began to undergo calcification and filling-in with streamer bone formation. The old cortex was adjoined to this new mass of bone. This response in the tibiae was not seen in the femora which were examined.

In light of the histologic analysis, one can view electrical stimulation according to the method described as promoting local bone formation. This formative process resembles the early development of the skeleton and its healing fracture callus counterpart. Wet weight and dry weight were enhanced as a result of cartilaginous proliferation. Ash weight was enhanced due to the calcification of the cartilage precursor. Ultimate stress was enhanced due to the favorable position of the responding material—i.e., towards the outer limits of the cortex. The outer position of the responding material increases the bone's aereal moment of inertia and enhances breaking strength.

The response seen in the femoral data indicates that some remote effects from electrical stimulation do occur. However, in order to see enhancement of ash weight in remote locations, higher voltages may be used.

TREATMENT OF EXISTING OSTEOPOROSIS

In this experiment, 18 animals had right-sided sciatic neurectomy performed on Day 1. After the neurectomy, the animals were not treated for 28 days so that a condition of osteoporosis would develop. In this experiment, essentially two control groups were used. A first control group of 6 animals was sacrificed 28 days after the neurectomy and provided a indication of the extent to which osteoporosis had occured as a result of the 28 days of immobilization. After the six animals of the first control group were sacrificed, determinations were made of the wet weight, dry weight, and ash weight of their tibiae and femora.

The remaining 12 animals had stainless steel electrodes 14 applied to the right tibia on day 28. However, only 6 animals of this group of 12 animals had a 10 volt peak-to-peak 60 KHz signal applied to the electrodes. The remaining 6 animals (second control group) acted as side-by-side sham controls (i.e. they where fitted with electrodes 14 but no stimulation signal was applied). On the twelfth day of stimulation (Day 40), these 12 animals (second control group and stimulated animals) were sacrificed.

Histological data analysis was undertaken in addition to the biomechanical testing and weighing. The histologic analysis consisted of sectioning in transverse the right immobilized tibia and femur and left-sided control tibia and femur of the animal. After dissection, the specimens were immediately sectioned on an Isomet sectioning machine the proximal and distal 2 mm of each bone being removed to allow the fixative to gain access to the medullary canal. Thereafter, each bone was sectioned on the Isomet machine with 5 equal 5-6 mm thick blocks. These specimens were labeled and fixed in 10% neutral buffered formalin for 24 hours. The fixative was then changed and the specimens were fixed for an additional 3 days in 10% neutral buffered formalin. The specimens were then washed for 2 hours in distilled water and then in 100 ml 95% ethanol with 5 drops of NH OH for 1 hour. Then the specimens were decalcified by the Villeneuva rapid decalcification solution consisting of 1.8 g NaCl, 25.5 ml distilled water, 59.5 ml 100% EtOH and 15 ml conc. HCl.

The specimens were dehydrated with two changes of saturated lithium carbonate for one hour each and three changes of distilled water, followed by 70% ethanol for 24 hours and then two changes of 70%, 80% and 95% alcohol. All specimens were then embedded in paraffin and sectioned in transverse section on a microtome. Two slides were prepared at each of the 5 successive levels, and the 5 consecutive transverse sections were stained with hematoxylin and eosin. The slides obtained were projected onto a Zeiss MOP3 magnetic board at 50× magnification, and then the cortical diameter, medullary canal diameter, cortical area, and percent porosity were determined for the right and left sides. Statistical significance was determined by comparing the R/L ratio in the control group to that of the experimental group by means of a "group t" test.

During cutting of the tibial specimens on the Isomet bone saw, duplicate 100 micron specimens were taken from the proximal metaphysis and mid-diaphysis for quantitative microradiography. The specimens were then placed in the X-ray cassette and exposures were made of the right and left sides on Kodak spectroscopic emulsion plates. The exposure settings of 25 MA, 10 KV for 10 minutes gave optimum results. The plates obtained were then quantitated on a Zeiss MOP3 apparatus for cortical area, cortical thickness, medullary canal area, total cross-sectional radius, and endosteal cross-sectional radius. An approximation to the aereal moment of inertia was obtained by the relationship $I = (\frac{1}{4})(r_0^4 - r_0^4)$ where $r_1$ is the cortical thickness and $r_0$ is the total cross-sectional radius. In addition, percent porosity was obtained by summing the area of the individual pores and then dividing this sum by the cortical area.

Results of this treatment experiment were tabulated and appear in Table III (tibiae) and Table IV (femora). Table III indicates that electrical stimulation at the tibia with a 10 volt peak-to-peak signal at 60 KHz results in statistically significant enhancement of tibial wet weight (FIG. 9), dry weight (FIG. 10), ash weight (FIG. 11), area of cortical bone (FIG. 12), and percent porosity (FIG. 13) when the tibial data from the stimulated group animals is compared to both the pre-stimulation (first control group) animals and sham (second control group) animals.

Figure 9:
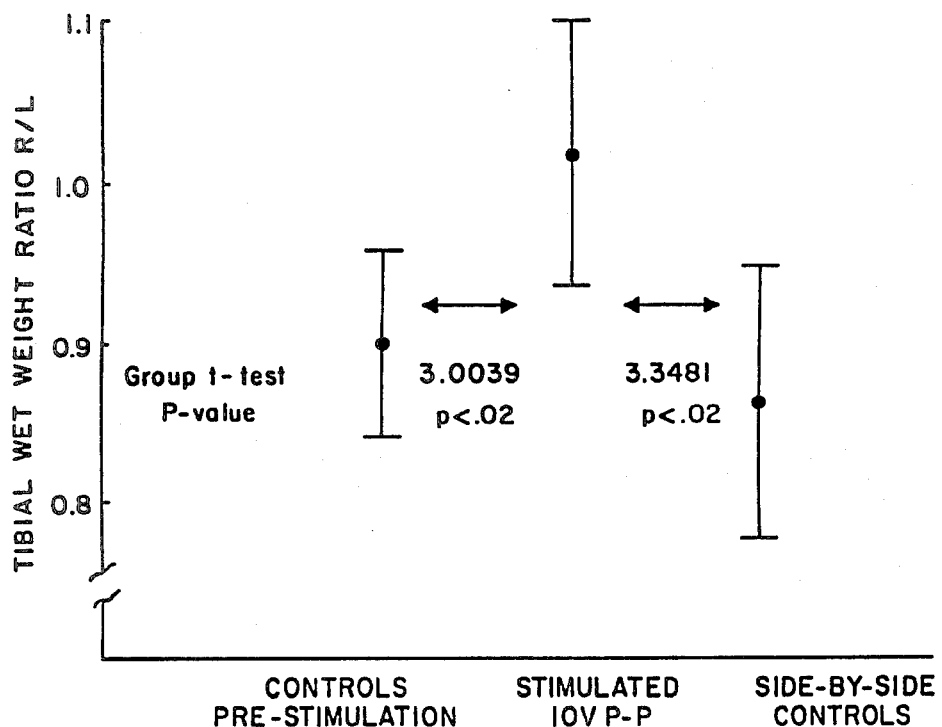
FIGS. 9-11, respectively, are graphs showing the tibial wet weight, the tibial dry weight and the tibial ash weight (ratio of right/left) of the stimulated (10 volt) group relative to the first and second control groups that were treated according to the invention.
Figure 10:
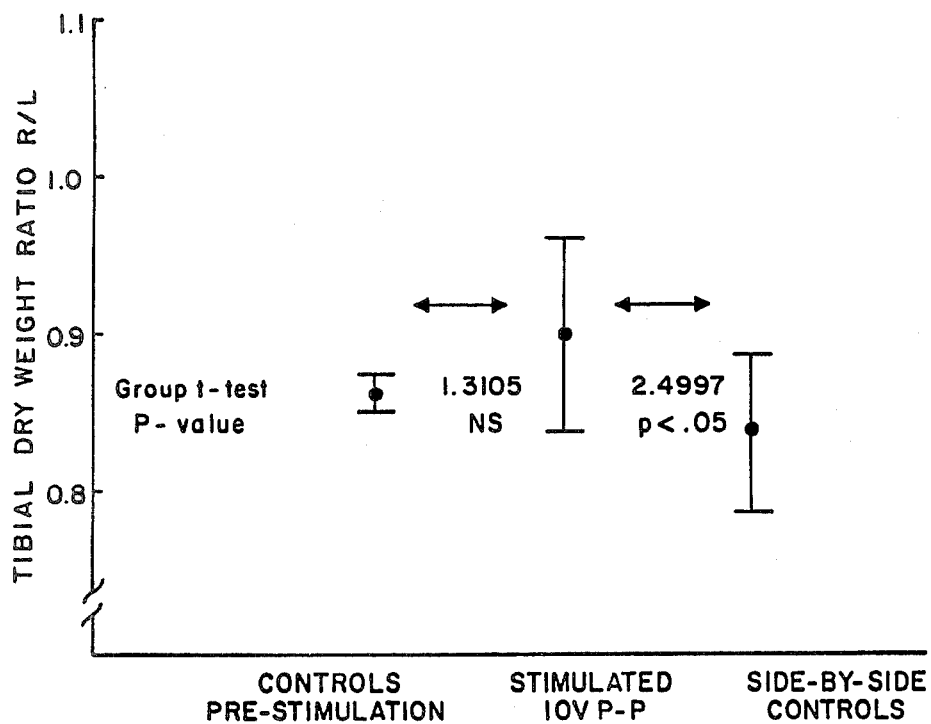
Figure 11:
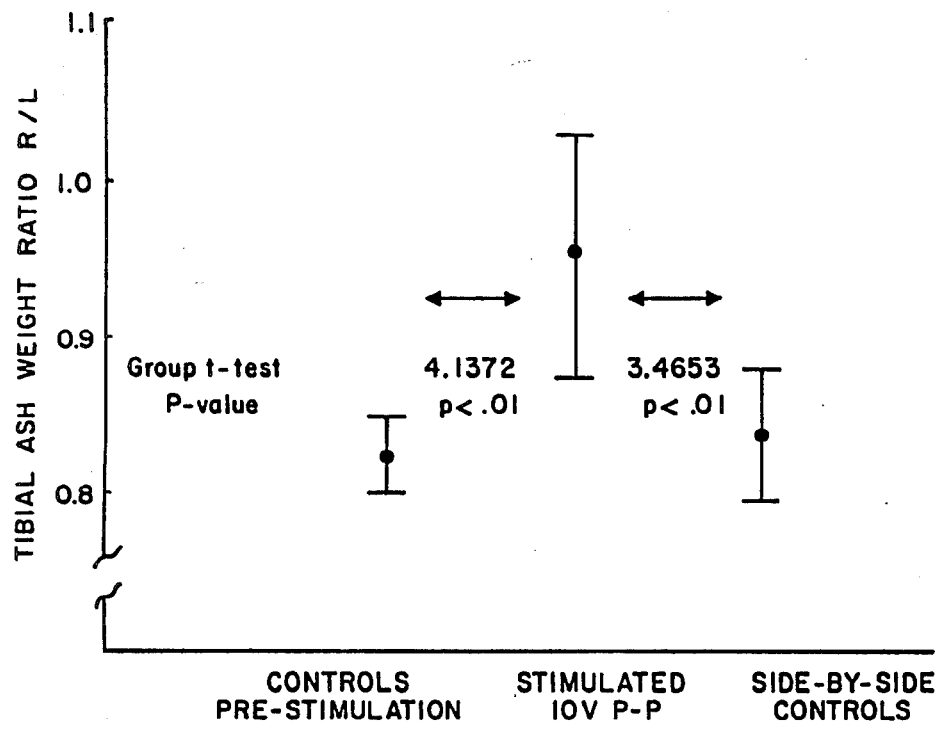
Figure 12:
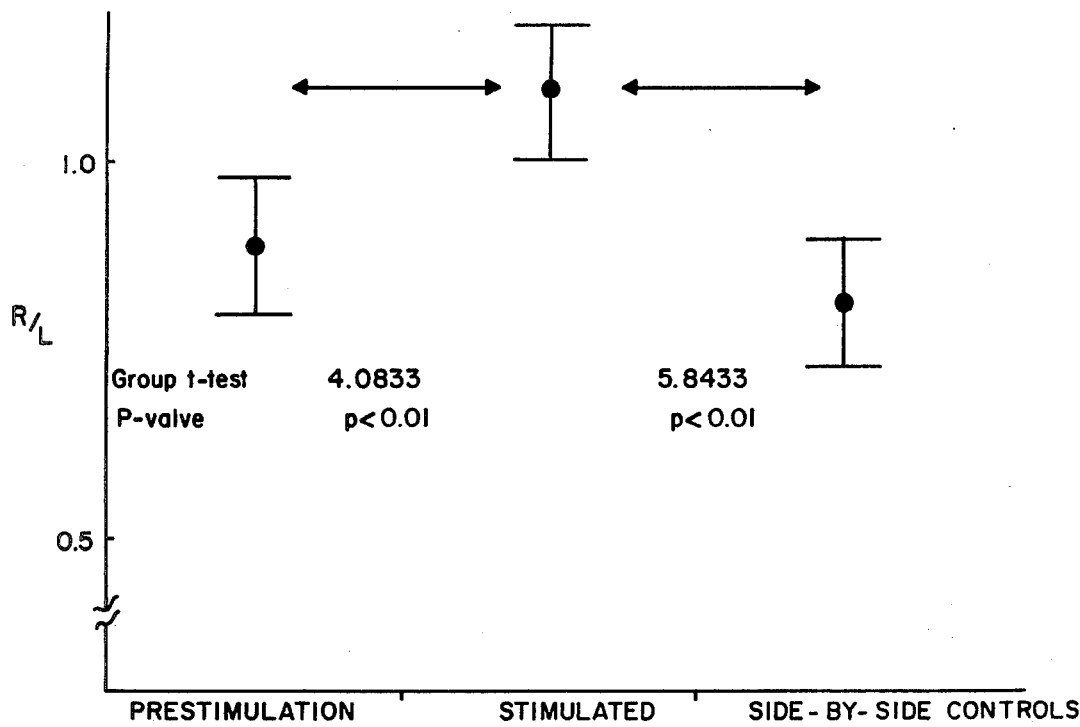
FIG. 12 is a graph showing the tibial % porosity of bone (ratio of right/left) of the stimulated (10 volt) group relative to the first and second control groups that were treated in accordance with the invention.

More specifically, as seen in FIG. 9, the tibial wet weight of the stimulated animals experienced a 16% increase and 20% increase over the first and second control groups, respectively. The tibial dry weight of the stimulated animals, as shown in FIG. 10, experienced a 2% increase and 10% increase over the first and second control groups, respectively. The tibial ash weight of the stimulated animals experienced a 16% increase and 14% increase over the first and second control groups, respectively, as illustrated in FIG. 11. Further as seen in FIG. 12, the total cortical bone area of the tibiae of the experimental group animals experienced a 20% increase and 34% increase over the first and second control groups, respectively.

Figure 13:
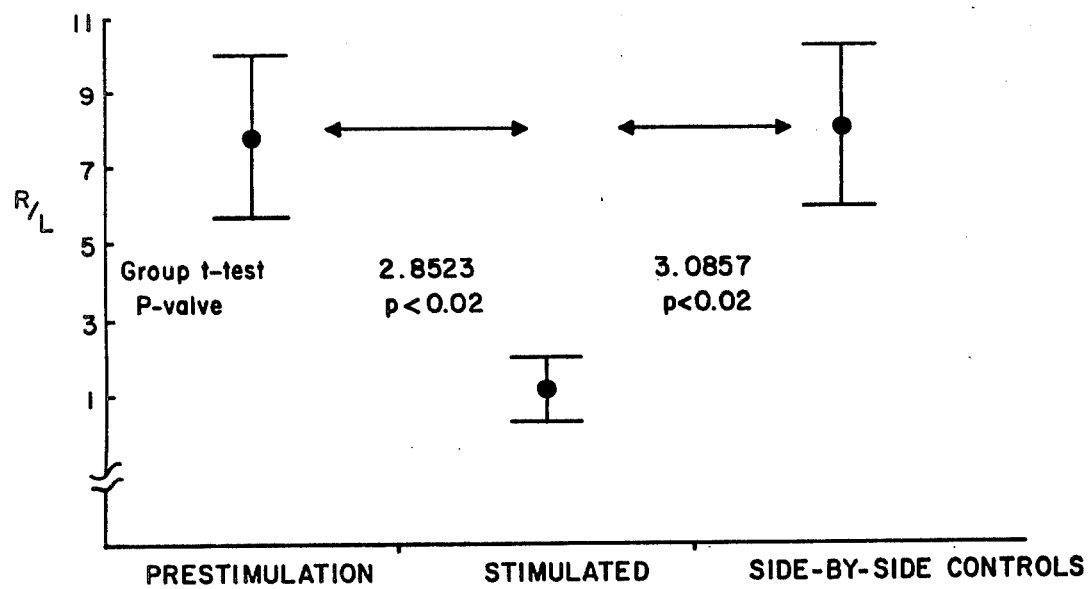
FIG. 13 is a graph showing the tibial total cross-sectional cortical bone area (ratio of right/left) of the stimulated (10 volt) group relative to the first and second control groups.

Lastly, as illustrated in FIG. 13, the tibial bone of the stimulated animals was significantly less porous than (only about 14% as porous as) the first and second control groups. However, as seen from Table III, the tibial

TABLE III

EXPERIMENT 2
TREATMENT OF DISUSE OSTEOROSIS USING 10 VOLT SIGNAL
TIBIAL DATA
(N = 6 IN EACH GROUP)

| | Controls (No Plates) Pre-Stimulation (Sacrificed at Day 28) | | | Experimental Stimulation (10V P-P) (Sacrificed at Day 40) | | | Controls (With Plates) Sham Controls (Sacrificed at Day 40) | | |
|---|---|---|---|---|---|---|---|---|---|
| | R | L | R/L | R | L | R/L | R | L | R/L |
| Wet Weight | 1.03332 ±0.05585 $p < .01$ | 1.14928 ±0.13016 | 0.90433 ±0.05888 | 1.22363 ±0.09829 NS | 1.17230 +0.10035 | 1.04702 +0.10036 $p < .02$ | 1.13245 +0.15985 $p < .05$ | 1.32960 +0.09675 | 0.86095 ±0.09197 $p < .01$ |
| Dry Weight | 0.44503 ±0.03777 $p < .001$ | 0.51205 ±0.04335 | 0.88687 ±0.02194 | 0.30155 ±0.03447 $p < .05$ | 0.55140 ±0.05556 | 0.90244 ±0.06275 $p < .02$ | 0.51025 ±0.04653 $p < .01$ | 0.60553 ±0.03180 | 0.82413 ±0.4032 $p < .05$ |
| Ash Weight | 0.23802 ±0.01948 $p < .001$ | 0.28790 ±0.02559 | 0.82456 ±0.01567 | 0.29675 ±0.03353 NS | 0.31130 ±0.03044 | 0.95417 ±0.07349 $p < .01$ | 0.27957 ±0.01662 $p < .001$ | 0.33433 ±0.01278 | 0.83622 ±0.03939 $p < .01$ |
| Ultimate Stress | 11.08474 ±1.61181 $p < .05$ | 15.21667 ±0.59801 | 0.73763 ±0.11265 | 12.03768 ±1.01422 $p < .05$ | 14.68333 ±0.28097 | 0.77714 ±0.06065 NS | 15.82028 ±2.17261 NS | 14.71667 ±0.4453 | 1.08803 ±0.14272 NS |
| Total Area | 29552.2 ±4596.3 NS | 32512.4 ±5644.2 | 0.91526 ±0.10039 | 34934.4 ±7257.5 NS | 35058.4 ±1145.3 | 1.00624 ±0.24129 NS | 29908.4 ±2683.6 NS | 35339.3 ±2521.4 | 0.84586 ±0.03559 NS |
| Area Cortical Bone | 17912.7 ±2113.9 $p < .02$ | 21870.8 ±2656.7 | 0.82033 ±0.04343 | 24289.0 ±6339.9 NS | 22855.3 ±1885.7 | 1.05959 ±0.23606 $p < .05$ | 19555.2 ±2244.0 $p < .01$ | 24697.4 ±2388.6 | 0.79167 ±0.04497 $p < .05$ |
| Area Medullary Canal | 11639.5 ±2912.5 NS | 10641.6 ±3127.8 | 1.12208 ±0.25233 | 10645.5 ±2094.8 NS | 12203.1 ±2382.5 | 0.89887 ±0.25736 NS | 10353.3 ±1332.9 NS | 10641.9 ±2008.5 | 0.98606 ±0.11274 NS |
| Porosity | 12.028 ±2.570 $p < .001$ | 1.897 ±0.721 | 7.74285 ±5.24381 | 2.007 ±0.882 NS | 1.847 ±0.181 | 1.04853 ±0.23086 $p < .02$ | 12.888 ±1.980 $p < .001$ | 1.899 ±0.700 | 7.92233 ±4.97065 $p < .02$ |
| Mean Cortical Thickness | 516.3 ±50.5 NS | 531.0 ±62.2 | 0.97802 ±0.10197 | 541.9 ±67.1 NS | 551.1 ±23.50 | 0.98692 ±0.15175 NS | 518.1 ±32.7 $p < .05$ | 561.5 ±32.4 | 0.92508 ±0.07676 NS |

TABLE IV

EXPERIMENT 2
TREATMENT OF DISUSE
OSTEOPOROSIS USING 10 VOLT SIGNAL
FEMORAL DATA
(N = 6 IN EACH GROUP)

| | Controls (No Plates) Pre-Stimulation (Sacrificed at Day 28) | | | Experimental Stimulation (10V P-P) (Sacrificed at Day 40) | | | Controls (with Plates) Sham Controls (Sacrificed at Day 40) | | |
|---|---|---|---|---|---|---|---|---|---|
| | R | L | R/L | R | L | R/L | R | L | R/L |
| Wet. Wt. | 1.51558 ±0.09465 NS | 1.65272 ±0.14249 | 0.91333 ±0.06481 NS | 1.64473 ±0.09297 NS | 1.74062 ±0.13000 | 0.94768 ±0.06398 NS | 1.75808 ±0.12787 NS | 1.88370 ±0.14264 | 0.9371 ±0.05427 NS |
| Dry Wt. | 0.64070 ±0.0704 NS | 0.78873 ±0.18550 | 0.84141 ±.07971 NS | 0.66332 ±0.05823 $p < .05$ | 0.73790 ±0.05723 | 0.89864 ±0.03112 NS | 0.72917 ±0.02797 $p < .001$ | 0.80205 ±0.03725 | 0.90338 ±0.02131 NS |
| Ash Wt. | 0.31733 ±0.03478 NS | 0.36297 ±0.03721 | 0.87388 ±0.02197 NS | 0.40722 ±0.15053 NS | 0.46723 ±0.14376 | 0.86166 ±0.04053 NS | 0.38907 ±0.01448 $p < .001$ | 0.43683 ±0.01796 | 0.89010 ±0.02295 NS |
| Ultimate Stress | 10.17537 ±2.06826 $p < .001$ | 15.125 ±1.13919 | 0.66809 ±0.09283 NS | 13.93568 ±3.08047 NS | 15.98333 ±0.59470 | 0.87133 ±0.18677 $p < .05$ | 14.29832 ±0.91256 NS | 15.31667 ±0.96212 | 0.95890 ±0.26446 | control group) animals.

ultimate stress, total cross-sectional area, medullary canal area and mean cortical thickness were not enhanced in the stimulated group when compared to both control groups.

In sum, the results indicated statistically significant enhancement of wet weight, dry weight, ash weight, area of cortical bone, and percent porosity in the stimulated tibia. These favorable results in the treatment experiment indicate that an existing osteoporosis condition in animal tibiae can be effectively treated using a 10 volt peak-to-peak stimulation signal at 60 KHz.

However, as can be seen in Table IV, no consistent statistically significant enhancement in any of the measured parameters was seen in the femur when stimulation was carried out over the tibial area. More specifically, the wet weight, dry weight, ash weight and ultimate stress R/L data for the experimental animals (middle column) was for the most part not significantly different than the R/L data for the first and second control groups at the right and left columns, respectively. Therefore, this data indicates that the effects of applying a treatment signal are relatively local.

Histologically, the stimulated tibiae exhibited a periosteal reaction with the periosteum being lifted off the cortex. As one moved away from the periosteum, the cartilage began to undergo calcification and filling-in with streamer bone formation. The old cortex was adjoined to this new mass of bone. This response was not seen in the femora which were examined. In light of the histologic picture, one can view stimulation in the manner described as promoting local bone formation. This bone forming process resembles the early development of the skeleton and its counterpart: healing fracture callus. Increases in wet weight and dry weight indicate cartilaginous proliferation, while increases in ash weight indicate calcification of the cartilage precursor. Diminution in percent porosity in the stimulated animals as compared to the controls indicates diminished resorption and increased bone formation. Since total cross-sectional area and medullary canal area were not enhanced in a statistically significant manner, while area cortical bone was enhanced, a combination of increased bone material synthesis and decreased bone material resorption was probably occuring.

Ultimate stress was not enhanced in the stimulated group as compared to the control groups. In fact, the sham controls (i.e. second control group) exhibited the highest ultimate stress, followed in decreasing order by the stimulated group and then the pre-stimulation controls. The use of a whole-bone test is complicated by the increased medullary canal size seen in the control groups as compared to the stimulated group. This trend is seen clearly in Table III. Consequently, the aereal moment of inertia is greater for the control groups than the stimulated group. This leads to the control bones breaking at a higher ultimate stress than the stimulated bones, when actually the weight and morphometric data in Table III show that the stimulated group has 20% more bone than either of the control groups and that this bone is only about 1/7 as porous.

In summary, the treatment as described not only arrested the existing osteoporotic condition, but it actually reversed the osteoporotic trend, and with certain treatment signals bone mass actually increased. Further, osteoporosis can be effectively prevented by applying a stimulation signal in accordance with the method of the invention, also as described above.

Also, since relatively little if any enhancement in the measured parameters was experienced for the femora, it appears that the effects of applying a stimulation signal are relatively local, and on this basis it appears that medical treatment of osteoporosis can be controlled to limit activity to selected body areas, at least to a degree.

It is to be understood that the invention is not limited to the precise method shown and described, and no limitation is intended or should be inferred. It can be appreciated that numerous variations and modifications may be effected without departing from the true spirit and scope of the novel concept of the invention. It is of course intended to cover by the appended claims all such modifications as fall within the scope of the claims.

I claim:

1. A non-invasive method of preventing and/or treating osteoporosis in bone in a living body comprising:
    applying electrodes to a treatment area on a body and
    supplying to said electrodes an alternating current stimulation signal in the ultrasonic frequency range of about 20 to 100 KHz to cause a current to flow in a body region affected by osteoporosis to thereby inhibit rarefication of bone mass.

2. The method in accordance with claim 1 wherein the peak-to-peak voltage amplitude of the generated signal is within the range of about 5 to 10 volts.

3. The method in accordance with claim 1 wherein the peak-to-peak voltage amplitude of the generated signal is about 10 volts.

4. The method in accordance with claim 1 wherein the frequency of the generated signal is about 60 KHz.

5. The method in accordance with claim 1 wherein the electrodes are bare metal electrodes in direct contact with the skin.

6. The method in accordance with claim 1 wherein the stimulation signal is a symmetrical sine wave.

7. The method in accordance with claim 1 wherein the stimulation signal is applied to the body substantially continuously.

8. A non-invasive method of preventing or treating osteoporosis in a living body comprising:
    applying electrodes to a treatment area of the body and
    supplying to the electrodes an alternating current stimulation signal having a generally symmetrical sine waveform and an amplitude of about 10 volts peak-to-peak at a frequency of about 60 KHz to cause a current to flow substantially continuously in a body region affected or likely to be affected by osteoporosis to thereby inhibit rarefication of bone mass.

* * * * *